(12) United States Patent
Bravo

(10) Patent No.: US 8,874,472 B2
(45) Date of Patent: Oct. 28, 2014

(54) METHODS AND APPARATUS FOR PRODUCE IDENTIFICATION USING TIME RESOLVED REFLECTANCE SPECTROSCOPY

(75) Inventor: Luis Eduardo Bravo, Atlanta, GA (US)

(73) Assignee: NCR Corporation, Duluth, GA (US)

( * ) Notice: Subject to any disclaimer, the term of this patent is extended or adjusted under 35 U.S.C. 154(b) by 706 days.

(21) Appl. No.: 12/570,064

(22) Filed: Sep. 30, 2009

(65) Prior Publication Data
US 2011/0078033 A1    Mar. 31, 2011

(51) Int. Cl.
| | |
|---|---|
| G06Q 20/00 | (2012.01) |
| G07G 1/00 | (2006.01) |
| G06Q 20/20 | (2012.01) |
| G06Q 30/06 | (2012.01) |
| G01N 21/47 | (2006.01) |

(52) U.S. Cl.
CPC .... *G01N 21/4795* (2013.01); *G01N 2021/4797* (2013.01); *G07G 1/0036* (2013.01); *G06Q 20/208* (2013.01); *G06Q 30/0603* (2013.01); *G06Q 20/202* (2013.01)
USPC ............................................. 705/23; 705/16

(58) Field of Classification Search
USPC ................................................... 705/16, 23
See application file for complete search history.

(56) References Cited

U.S. PATENT DOCUMENTS 6,069,696 A *   5/2000   McQueen et al. ............ 356/326
6,446,869 B1 *  9/2002   Seevers et al. ........... 235/462.43

OTHER PUBLICATIONS

Cubbedu, et al. "Measuring Fresh Fruit and Vegetable Quality: Advanced Optical Methods," appearing in *Fruit and Vegetable Processing: Improving Quality*, Ed. Jongen, Wim, Woodhead publishing (2001) pp. 150-169.

* cited by examiner

*Primary Examiner* — Ramsey Refai
(74) *Attorney, Agent, or Firm* — Peter H. Priest; Joseph P. Merhle

(57) ABSTRACT

Systems and techniques for produce identification for transaction processing. A produce item to be entered into a transaction is identified using time resolved reflectance spectroscopy. A produce item is injected with laser light over a selected range of wavelengths, and light emitted from the produce item is detected and measured over time. The measurement is processed to generate absorption and scattering spectra for the produce item. The absorption and scattering spectra are compared against those of known produce items, and upon determination that an acceptable match has been achieved, a transaction record is updated with information relating to the produce item.

16 Claims, 2 Drawing Sheets

METHODS AND APPARATUS FOR PRODUCE IDENTIFICATION USING TIME RESOLVED REFLECTANCE SPECTROSCOPY

FIELD OF THE INVENTION

The present invention relates generally to improved systems and techniques for product identification in retail transactions. More particularly, the invention relates to systems and techniques for detecting time resolved reflectance spectroscopy properties of produce and comparing the detected properties against stored information relating to known time domain resolved reflectance spectroscopy properties of the items.

BACKGROUND OF THE INVENTION

The increased use of automation in transaction processing has led to substantially increased efficiency and reduced costs in many applications, including supermarket transaction applications. Many products are packaged or otherwise presented so that standardized identifiers, such as bar codes, can be read by automated equipment. However, produce has been and continues to be particularly resistant to automated identification by prior art techniques. Produce identification frequently relies on books or charts of photographs available to a cashier, matching by a customer or cashier of the appearance of a produce item to a photograph on a checkout terminal display, knowledge by a cashier of the identities of various produce items, labels on each piece of produce, or any of a number of other mechanisms involving manual selections or entries by a cashier or customer. Such procedures involve labor costs to a retailer and in the case of self service entries, increase the time spent by the customer in completing a transaction. In addition, the use of labels directly affixed to food items has created its own particular difficulties since its inception. The affixing of labels to food items adds costs due to the labor or machinery needed to affix the labels, and the presence of labels on food items frequently decreases customer satisfaction. In addition, not every produce item is conducive to the use of labels.

SUMMARY OF THE INVENTION

According to one aspect, the present invention addresses such problems, as well as others, by providing systems and techniques that recognize produce items based on their chemical compositions. One particularly promising technique for determining characteristics of produce items is time resolved reflectance spectroscopy. Time resolved reflectance spectroscopy involves recognition that light injected into a turbid medium involves scattering and therefore photon migration. A light pulse injected into a medium is reemitted over time, and the intensity of the light reemitted typically diminishes as absorption of scattered light within the medium reduces the reemission of light from the medium. The detected light intensity over time may be referred to as a temporal profile, and the temporal profile can be analyzed to generate scattering and absorption spectra.

The use of time resolved reflectance spectroscopy to analyze properties of fruits and vegetables is described by Cubbedu, Pifferi, Taroni, and Toricelli, "Measuring Fresh Fruit and Vegetable Quality: Advanced Optical Methods," appearing in *Fruit and Vegetable Processing: Improving Quality* Ed. Jongen, Wim, Woodhead publishing (2001) pp. 150-169. (Cubbedu et al.), which is incorporated herein by reference in its entirety.

The present invention takes advantage of the fact that absorption and scattering properties of produce items can exhibit distinctive characteristics due to the chemical makeup of the produce items, and absorption and scattering spectra resulting from the presence and amount of particular components will be consistent in examples of produce items having the same components in the same quantity. Therefore, a collection of scattering and absorption signatures can be produced and stored, and used for comparison against a produce item to be identified.

A transaction terminal according to an aspect of the present invention therefore includes a produce identifier employing time domain reflectance spectroscopy. One or more produce items submitted for purchase is appropriately illuminated and light emitted back from the items as a result of the illumination are detected. The detected light is analyzed to compute a time reflectance spectroscopy signature for the submitted item, including absorption and scattering signatures. Special note is taken of the presence and level of peaks and the signature is compared against a collection of stored signatures. Upon determination that the computed signature matches a stored signature within predetermined limits, the terminal determines that identification has been successful. The name and image of the item may be presented to the user, such as a customer or operator, as a further check on the identification, with the user being allowed to accept or reject recognition of the item.

A more complete understanding of the present invention, as well as further features and advantages of the invention, will be apparent from the following Detailed Description and the accompanying drawings.

DETAILED DESCRIPTION

Figure 1:
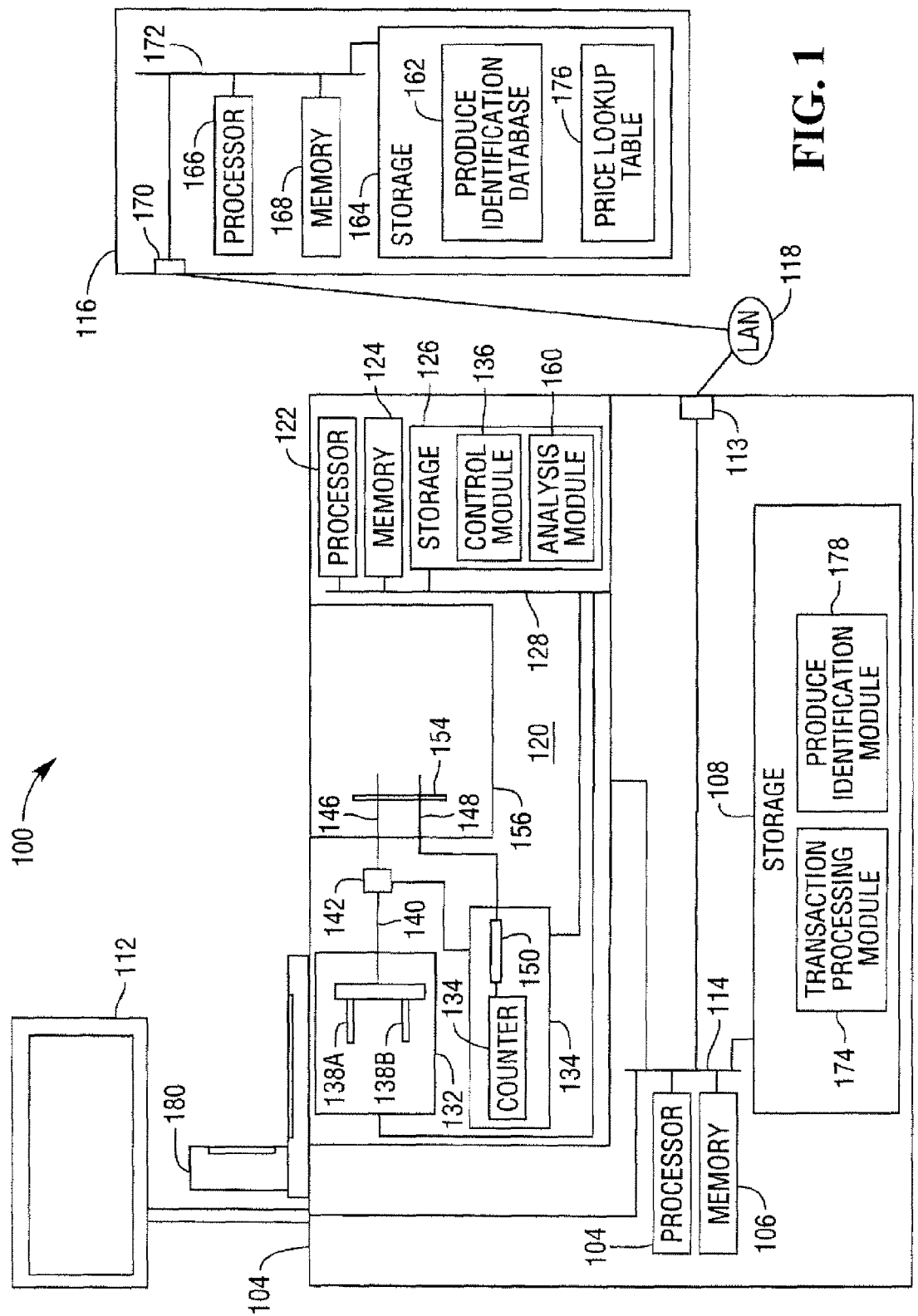
FIG. 1 illustrates a transaction processing system according to an aspect of the present invention.

FIG. 1 illustrates a transaction processing system 100 according to an aspect of the present invention. The system 100 includes a transaction terminal 102, operating under the control of a processor 104. The terminal 102 further includes memory 106, long term storage 108, a user interface 112, which may be a touch screen display, and a network interface 113, communicating over a bus 114. The terminal 102 communicates with a central server 116 over a network, such as a local area network 118.

The terminal 102 also includes a produce analyzer 120, which employs time resolved reflectance spectroscopy. The produce analyzer 120 injects light into produce samples to be identified in order to cause the sample to re-emit the light. The re-emitted light is detected and analyzed in order to generate absorption and scattering spectra for the sample. The absorption and scattering spectra are compared against stored absorption and scattering spectra for known produce items. The absorption and scattering spectra are stored in association with identifications of the known produce items that they characterize.

The produce analyzer 120 employs its own processor 122, memory 124, and storage 126, communicating over a bus 128. The produce recognition module 130 further employs a light source 132 and a light detector 134, with the light source 132 and light detector 134 operating as directed by the processor 122. The produce analyzer 120 may suitably operate under the direction of a control module 136, implemented as software residing in storage 126 and transferred to memory 124 as needed for execution by the processor 122.

The produce analyzer 120 injects light into produce items to be identified by counting the number of photons received by the light detector 134 over time and processing the count information to generate absorption and scattering spectra for the item under examination. The light source 132 is capable of injecting light into a sample under examination, resulting in the migration of photons within the medium and the increasing absorption of photons over time.

An exemplary arrangement that may be employed is described in. Cubbedu et al., 155-157. The light source 132 may suitably comprise a set of pulsed laser sources 138A and 138B. The pulsed laser sources 138A and 138B are chosen to provide a desired range of wavelengths. Different produce items may produce spectra exhibiting similar features at some wavelengths, and differing features and other wavelengths, and the laser sources 138A and 138B are preferably chosen so that a sufficient range of wavelengths will be employed that spectra will be produced exhibiting sufficient distinctive features that different produce items can be distinguished. Two exemplary laser sources are illustrated here, with the source 138A employing a wavelength of 672 nanometers (nm) and the source 138B employing a wavelength of 800 nm. The pulse duration of the sources 138A and 138B is 100 picoseconds (ps), and the repetition rate is up to 80 megaHertz (MHz).

Light generated by the pulsed laser sources 138A-138C is preferably coupled into an optical fiber 140. The optical fiber 140 feeds into a fiber optic splitter 142, which directs approximately 5% of the signal to the detector 134 and approximately 95% of the signal to an injection fiber 146, which conveys this 95% of the signal to the produce item. The 5% of the signal received at the detector 134 serves to account for time drifts and to provide a time reference. The detector 134 is fed by a collector fiber 148, and may suitably comprise a photomultiplier tube 150 detecting emissions from the produce item, with the tube 150 feeding a single-photon counter 152.

The injection fiber 146 and the collector fiber 148 are maintained in position by a holder 154, which maintains the fibers 146 and 148 in parallel. A produce item may be placed in a receptacle 156, in contact with the fibers 146 and 148, allowing for direct injection of light and collection of emitted light.

The produce analyzer 120 analyzes the temporal profile of the light emission from the produce item using the radiative transport equation under the diffusion approximation for a semi-infinite homogenous medium. As explained by Cubbedu et al., this equation is as follows:

$$R(\rho, t) = \frac{1}{2}(4\pi v)^{-3/2} t^{-5/2} e^{-\mu_a v t} e^{\frac{\rho^2}{4Dvt}} \left( z_0 e^{\frac{z_0^2}{4Dvt}} - (z_0 + 2z_c) e^{\frac{(z_0 + 2z_c)^2}{4Dvt}} \right)$$

$R(\rho,t)$ is the number of photons per unit time (t) and area re-emitted from the tissue at a distance $\rho$ from the injection point. $\rho$ is the distance between the injection fiber 146 and the collecting fiber 148. $v=c/n$ is the speed of light in the medium. n is the refraction index. $D=(3\mu_s')^{-1}$ is the diffusion coefficient, $z_0=(\mu_s')^{-1}$ is the isotropisation length, and $z_0$ is the extrapolated distance that takes into account the refraction index mismatch at the surface. The processor 122 operates under the control of an analysis module 160 to perform curve fitting according to the theoretical function, using the photon count over time and the known parameters, and the fitted curves are then analyzed to determine absorption and scattering properties of the item. Absorption properties include the absorption coefficient versus wavelength of injected light, and scattering properties include the scattering coefficient versus wavelength of injected light. The absorption and scattering properties of different items vary according to the chemical composition of the items, and such variations can be employed to identify produce items.

The server 116 therefore stores a produce identification database 162 comprising a record for each produce item that can be identified by the produce analyzer 120. The database 162 is hosted in storage 164, and the server 116 further employs a processor 166, memory 168, network interface 170, and bus 172.

Each record in the database 162 includes information such as item name, price, identification code, and other relevant information. Each record also includes information representing an optical signature of the item. Such information may include scattering and absorption spectra, comprising scattering and absorption coefficients for light injected over a range of wavelengths. The wavelengths are chosen to detect differing chemical composition of differing items, and thus to distinguish the items. Absorption spectra of chemical components often exhibit greater or lesser absorption coefficients at particular wavelengths, and differing items of produce will typically contain similar quantities of many components. Thus, many items will exhibit absorption spectra that exhibit peaks at similar wavelengths characteristic of chemical components they share in similar quantities. However, other chemical components will exist in differing quantities between items, resulting in absorption and scattering coefficients that differ between items at wavelengths characteristic of chemical components whose quantities differ between items.

The server 116 therefore stores absorption and scattering spectra for each produce item to be identified. Each record stored in the database 162 includes information relating to an absorption spectrum and a scattering spectrum representative of the produce item with which the record is associated.

The terminal 100 employs a transaction processing module 174, suitably implemented as software residing in storage 108 and transferred to memory 106 as needed for execution by the processor 104. As items are presented for entry into the transaction, relevant information is retrieved from a repository, such as a price lookup table 176, and a transaction record is updated. When a produce item is presented that is to be identified, the transaction processing module 174 communicates with the control module 136 to activate the produce analyzer 120.

When the produce analyzer 120 is activated, the control module 136 activates the light source 132 and the light detector 134. The light source 132 injects light into the item, with appropriate ones of the lasers 138A and 138B being activated to provide illumination at desired wavelengths. For each of the lasers that is activated, the light detector 134 counts the photons conveyed to the detector 134 by the collector fiber 148, and supplies a count per time interval to the processor 122. The processor 122, under the control of an emission analysis module 156, analyzes the photon count over time for each wavelength and generates absorption and scattering spectra for the item. The control module 136 communicates the absorption and scattering spectra to the transaction processing module 174, which invokes a produce identification module 178 to use the absorption and scattering spectra to match the produce item to a record corresponding to the produce item. The produce identification module 178 examines the absorption and scattering spectra to identify distinctive characteristics that can be used for matching. Such characteristics may include overall curve shape, as well as peaks or troughs representing higher or lower absorption or scattering values at different wavelengths. Characteristics that may be chosen may include each distinctive absorption value, and the wavelength at which it is exhibited, as well as each distinctive scattering value, and the wavelength at which it is exhibited. Other characteristics may include ratios between characteristics appearing at different wavelengths, to take into account the fact that the presence and thickness of skin may alter the absorption values at each wavelength while preserving the overall shape of the spectrum.

The illumination of an item and detection of the light emitted from that item, will produce characteristics typical of chemical components making up an item, and will provide distinctive features for matching against known produce items.

Once the absorption and scattering spectra analyzed and distinctive features have been identified, the produce identification module 178 consults the produce identification database 162, and matches distinctive features of absorption and scattering spectra for the item being examined against known stored features associated with produce items whose records are stored in the database 162. If matching is accomplished against one item with a sufficient degree of certainty, the item is identified and the item identification is provided to the transaction module 174. If a match against a single item cannot be accomplished, but isolation to a specified number of items can be accomplished, the possible matches may be presented to a user or operator, who may then conduct further investigation to determine the identity of the item. If identification cannot be accomplished, an appropriate notification is provided to a user or operator, who may then use other mechanisms to identify the item. Once identification is provided to the transaction processing module 174, the transaction processing module 174 enters updates a transaction record with appropriate information, such as item identification, item price, item weight or number of units, and other desired information, into a transaction record. The transaction processing module 174 then proceeds with the transaction. The results of the resolution of a failure of identification or the resolution of an ambiguity may be compiled and used to provide a learning capability for the produce identification module 178. For example, absorption and scattering spectra associated with a failed or ambiguous identification may be stored along with the actual identification of the produce item produced by alternative mechanism for identification, and characteristics associated with such stored absorption and scattering spectra may be used to enhance the stored absorption and scattering information associated with the produce item identified using the alternative mechanism.

A system such as the system 100 will typically implement a number of mechanisms for entering information relating to products, and information made available through the use of these mechanisms may be used by the produce identification module 178 to supplement information generated by the produce analyzer 120. For example, the system 100 may employ a scanner/scale combination 180 for reading bar codes and weighing items such as produce items. Once absorption and scattering spectrum information has been delivered by the produce analyzer 178, this information may be evaluated in light of additional information provided by the scanner/scale combination 180. A produce item may be placed on the scanner/scale combination 180 for weighing, and if the weight of the produce item does not conform to an expected weight for an item corresponding to the information provided by the produce analyzer 120, the transaction processing module 174 can report the anomaly and request clarification. For example, if the produce analyzer provides information associated with a grapefruit, but the weight of the item is less than a grapefruit is expected to weigh, the transaction processing module 174 may prepare a message reporting the identity if the item as detected by the produce analyzer 120 and report that the detected weight does not conform to expectations. Weight information may also be employed to help resolve ambiguities. For example, if the produce analyzer 120 provides information that may be associated with either of two possible items, one weighing substantially more and one weighing substantially less, the produce identification module 178 may use weight information to identify the item.

The scanner scale combination 180 may provide imaging capabilities, and such capabilities may be employed to supply image information to the produce identification module 178, which may employ such information to improve produce identification. For example, the scanner/scale combination 180 may provide image scanning capabilities such as are typically used for capturing and processing bar codes, and image capture may be performed using an imaging device as known in the art. The scanner/scale combination 180 may be configured such that an operator is allowed to choose to capture a complete image of an object in a field of view of a scan window. The produce identification database 162 may include image information for each item, as well as the information relating to the absorption and scattering spectra for the item. Comparisons of image information for an item against image information stored in the database 162 can be correlated against comparisons of the absorption and scattering spectra for an item against stored information. Correlation can be performed between the results of the comparisons, helping to identify discrepancies and resolve ambiguities. Alternative mechanisms for the use of image information to enhance produce identification may employ detection of reflected light produced as a result of optical scanning. Proper analysis of such reflected light may provide information relating to the size and shape of an object, and size and shape information may be stored in the database 162 for use in combination with information provided by the produce analyzer 120. Exemplary systems and techniques relating to the use of image information provided by optical scanning are discussed in Mergenthaler et al., U.S. Pat. No. 7,059,527, assigned to the assignee of the present invention and incorporated herein in its entirety.

Figure 2:
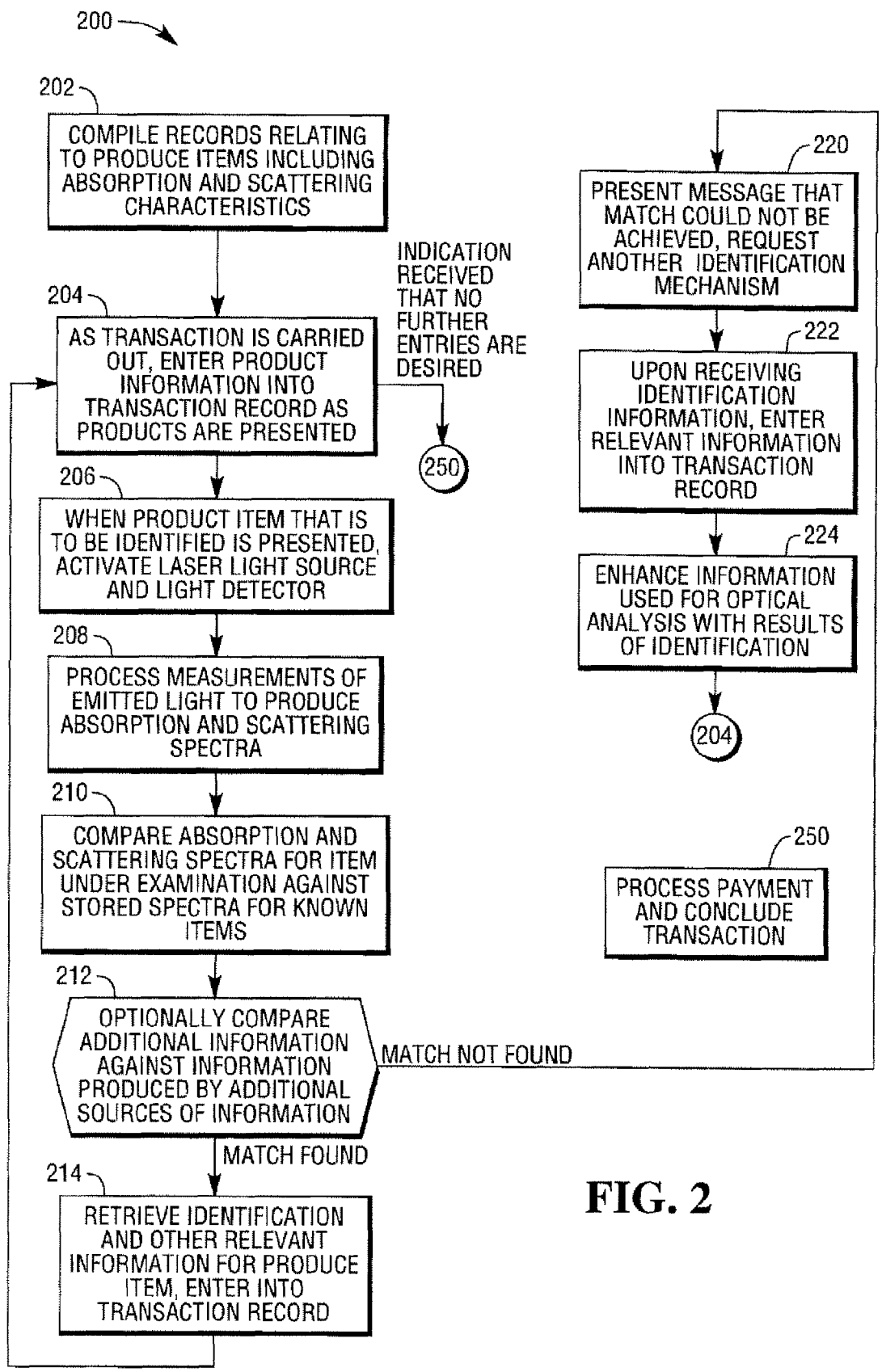
FIG. 2 illustrates a process of transaction processing according to an aspect of the present invention.

FIG. 2 illustrates the steps of a process 200 according to the present invention. The process 200 may suitably be carried out using a system such as the system 100 of FIG. 1. At step 202, a set of records relating to produce items is compiled. Each record includes information such as item identifier, description, and price, and also includes optical characteristics used to identify the item. At step 204, as a transaction at a point of sale terminal is carried out, product information is entered into a transaction record as products are presented at the terminal. When an indication is received that no further transaction entries are desired, the process proceeds to step 250.

At step 206, when a produce item that is to be identified is presented, a produce analyzer comprising a laser light source and a light detector is activated. The light source injects laser light over a selected range of wavelengths into the produce item, and the light detector receives light emitted from the produce item. Because a produce item is a turbid medium, light is subjected to absorption and scattering, and the absorption and scattering can be evaluated by measuring the light emitted over time, using time resolved reflectance spectroscopy. Therefore, light from the produce item s captured and fed to a measuring device, such as a detector in combination with a photon counter. At step 208, the measurements of the light emitted from the produce item are processed to generate absorption and scattering spectra, and at step 210, the absorption and scattering spectra are compared against stored absorption and scattering spectra associated with known produce items. Comparison may include examining absorption and scattering spectra for distinctive features, such as peaks occurring at particular wavelengths, or overall average values, and performing an initial search for spectra sharing those features, and then doing more detailed examination of spectra selected as a result of the initial search. At optional step 212, identification information produced by the examination and comparison of absorption and scattering spectra is compared against additional sources of information, such as weight and image information.

If absorption and scattering spectra associated with a single item are found matching the absorption and scattering spectra for the item under examination within predetermined limits, and anomalies produced by comparison with additional information are not detected, the process proceeds to step 214. If an unambiguous match cannot be found, the process skips to step 220.

At step 214, identification information and other relevant information for the identified produce item is retrieved and entered into a transaction record. The process then returns to step 204.

At step 220, a notice is presented that an unambiguous match to a known produce item cannot be achieved and requesting use of an alternative identification mechanism, such as manual entry of a code or other identification information. At step 222, upon entry of appropriate identification information, identification and other relevant information is entered into the transaction record. At step 224, the information used to perform identification using analysis of absorption and scattering spectra is refined using the results of the alternative identification mechanism.

The process then returns to step 204.

At step 250, reached after an indication that no further transaction entries are desired, a transaction total is presented, payment is processed, and the transaction is concluded.

While the present invention is disclosed in the context of a presently preferred embodiment, it will be recognized that a wide variety of implementations may be employed by persons of ordinary skill in the art consistent with the above discussion and the claims which follow below.

I claim:

1. A point of sale transaction processing terminal comprising:
    a user interface for receiving user inputs relating to items presented for entry into a transaction;
    a produce analyzer for identifying a produce item presented for entry into a transaction, the produce analyzer being operative to inject pulsed laser light into a produce item presented for identification and detect light emitted from within the produce item in response to the injected pulsed laser light, the produce analyzer being operative to measure the light emitted over time and process the measurement of light emitted over time to generate time resolved reflectance spectroscopy absorption and scattering spectra for the produce item, the produce analyzer being operative to compare the absorption and scattering spectra for the produce item against absorption and scattering spectra of known produce items and identify the produce item if the absorption and scattering spectra match a those of a known produce item within predetermined limits, and using one or more ratios between characteristics of the spectroscopy absorption and scattering spectra for ratios relevant to the characteristics of the produce item presented to account for a presence and a thickness of skin associated with the produce item presented; and
    a processor for receiving the identification of the produce item from the produce analyzer and updating a transaction record with information relating to the produce item.

2. The terminal of claim 1, further comprising a remote interface to a server storing a produce identification database comprising a plurality of records, each record including identification information for a produce item in association with absorption and scattering spectrum information for the produce item, and wherein the produce analyzer compares the absorption and scattering spectra for the produce item to be identified against absorption and scattering spectrum information stored in the database.

3. The terminal of claim 2, wherein the produce analyzer examines the absorption and scattering spectra of the produce item to be identified to identify distinctive characteristics and initially searches the database to retrieve records including absorption and scattering spectrum information exhibiting similar characteristics, the produce analyzer further examining the absorption and scattering spectrum information in the retrieved records to further compare the information against the absorption and scattering spectra of the produce item to be identified.

4. The terminal of claim 3, wherein distinctive characteristics include absorption peaks at particular wavelengths.

5. The terminal of claim 1, wherein if the produce analyzer cannot unambiguously identify the produce item, the processor presents a message requesting a user to employ an alternative identification mechanism.

6. The terminal of claim 5, wherein the results of one or more alternative identification mechanisms are combined with information generated by the produce analyzer to refine stored information used by the produce analyzer for identification.

7. The terminal of claim 1, wherein the processor is operative to receive weight information relating to the produce item and to correlate produce identification information received from the produce analyzer against the weight information to refine identification of the produce item.

8. The terminal of claim 1, wherein the processor is operative to receive image information relating to the produce item and to correlate produce identification information received from the produce analyzer against the image information relating to the produce item.

9. A method of point of sale transaction processing, comprising the steps of:
    receiving, at a point of sale terminal, user inputs relating to items presented for entry into a transaction;
    upon receiving an indication that a produce item has been presented for entry into the transaction, activating one or more pulsed laser sources and an emitted light detector of a produce analyzer;
    controlling the one or more pulsed laser sources to inject pulsed light into the produce item over a specified range of wavelengths;
    measuring light emitted from within the produce item over time wherein the light emitted is a response to the pulsed laser light injected into the produce item;
    controlling a processor of the produce analyzer to generate time resolved reflectance spectroscopy absorption and scattering spectra for the produce item from the measured emitted light;

identifying, by the processor one or more ratios between characteristics of the spectroscopy absorption and scattering spectra for ratios relevant to the characteristics of the produce item to account for a presence and a thickness of skin associated with the produce item;

controlling the processor of the produce analyzer to compare the absorption and scattering spectra for the produce item against absorption and scattering spectrum information for known produce items; and upon detecting a match between the absorption and scattering spectra for the produce item and absorption and scattering spectrum information for a known produce item, identifying the produce item to be identified as a sample of the known produce item; and updating a transaction record with information relating to the known produce item.

10. The method of claim 9, wherein the step of comparing the absorption and scattering for the produce item against absorption and scattering spectrum information for known produce items comprises communicating with a remote server to retrieve records from a database storing identification information for known produce items in associated with absorption and scattering spectrum information for the known produce items.

11. The method of claim 10, wherein the step of comparing the absorption and scattering for the produce item against absorption and scattering spectrum information for known produce items comprises identifying distinctive characteristics of the absorption and scattering spectra for the produce item and initially searching the database to retrieve records including absorption and scattering spectrum information exhibiting similar characteristics, and further examining the absorption and scattering spectrum information in the retrieved records to further compare the information against the absorption and scattering spectra of the produce item.

12. The method of claim 11, wherein the distinctive characteristics include absorption peaks at particular wavelengths.

13. The method of claim 9, further comprising a step of receiving weight information for the produce item and comparing the weight information with identification information based on examination of absorption and scattering spectra and refining identification based on the comparison.

14. The method of claim 9, further comprising a step of receiving image information for the produce item and comparing the weight information with identification information based on examination of absorption and scattering spectra and refining identification based on the comparison.

15. The method of claim 9, wherein if the produce analyzer cannot unambiguously identify the produce item, the processor presents a message requesting a user to employ an alternative identification mechanism.

16. The method of claim 15, followed by a step of combining the results of one or more alternative identification mechanisms with absorption and scattering spectrum information for the item under examination to refine stored information employed for identification using absorption and scattering spectra.

\* \* \* \* \*